United States Patent [19]

Shults

[11] Patent Number: Plant 5,651

[45] Date of Patent: Jan. 28, 1986

[54] APRICOT TREE—HOMEDALE CULTIVAR

[75] Inventor: Garfield Shults, Homedale, Id.

[73] Assignee: Stark Brothers Nurseries & Orchards Company, Louisiana, Mo.

[21] Appl. No.: 602,673

[22] Filed: Apr. 23, 1984

[51] Int. Cl.[4] ..... A01H 5/00

[52] U.S. Cl. ..... Plt./39

[58] Field of Search ..... Plt./39

*Primary Examiner*—James R. Feyrer

*Attorney, Agent, or Firm*—Burns, Doane, Swecker & Mathis

[57] ABSTRACT

A new and distinct apricot variety which has an extended bloom period and is somewhat spring frost tolerant is provided. The tree is very productive, spreading, hardy, and self-pollinating. The medium sized fruit of this new variety ripens over a relatively long period and is juicy, meaty textured, deliciously flavored, and has an orange skin with an attractive bright red blush. The fruit also has an edible sweet kernel.

1 Drawing Figure

SUMMARY OF THE INVENTION

The new and distinct apricot variety of the present invention originated as a chance seedling in the cultivated state in my orchard at Homedale, Id. Since apricot trees of the Wilson Delicious variety (sometimes called the Victoria variety) were growing nearby, it is likely that the new variety is related to such previously known variety. The new variety was discovered by me in the spring of 1970, and was observed to bloom later than trees of the Wilson Delicious variety, the Roberts variety (U.S. Plant Pat. No. 674), and the Hungarian Rose variety growing in the same general area.

The apricot tree of the new variety also was observed to exhibit the following combination of characteristics:

(a) a medium-small spreading growth habit, (b) an extended bloom period, (c) enhanced spring frost tolerance, (d) abundantly forms deliciously flavored medium-sized quality fruit which is meaty textured and juicy and bears an attractive orange skin color having a bright red blush, and (e) forms a sweet edible almond-type kernel. Scionwood of the new variety was sent to Louisiana, Mo. for propagation and testing soon after the attractive fruit first was observed.

The original tree at Homedale, Id., has continued to bloom over an extended period of time each year. This characteristic has prevented the late blooming flowers from being injured by late spring frosts. It has been shown that the new variety is capable of self-pollination by bagging the blooms so as to eliminate the possibility of cross-pollination. The original tree has been observed to bear abundant crops annually which ripen over a relatively long period of time (e.g., up to about 14 days). The above characteristics also have been confirmed following asexual propagation by budding and by observing trees grown at Louisiana, Mo.

When the new variety is compared to the Wilson Delicious variety, it is generally observed to be more productive, to form larger fruit, and to bloom over a longer period of time.

The new variety of the present invention has been named the Homedale cultivar, and is being marketed by Stark Brothers, Nurseries and Orchards Company under the Stark and Double Delight trademarks.

BRIEF DESCRIPTION OF THE PHOTOGRAPH

The accompanying photograph shows typical specimens of the fruit and foliage of the new apricot variety in color as nearly true as it is reasonably possible to make the same in a color illustration of this character.

DETAILED DESCRIPTION OF NEW VARIETY

The following is a detailed description of the new variety where color terminology is to be accorded its ordinary dictionary significance except where otherwise inicated. The specimens described were grown at Homedale, Id.

Representative dates of first and last pickings at Homedale, Id. are July 12 and July 23.

Tree: Medium small; vigorous; open; spreading; vase formed; hardy; very productive; regular bearer.

*Trunk.*—Size: Medium stocky.

*Branches.*—Size: Medium stocky. Color: Brown. Lenticels: Numerous in number and large in size.

*Leaves.*—Size: Medium large, medium thick, approximately 2⅞ inches in length and approximately 2⅜ inches in width. Form: Ovate, and acutely pointed. Color-Upper Surface: Hays Green Plate XVIII, Color No. 33 — Tone k of Ridgeway's Color Standards. Color-Lower Surface: Shamrock Green — Plate XXII, Color No. 33″ — tone i of Ridgeway's Color Standards. Margin: Glandular, and finely serrate. Petiole: Medium long, and medium thick. Glands: Alternate, 4 to 7 in number, globose.

Flowers: Representative dates of first and full blossoms at Homedale, Id. are March 15 and March 20 respectively; flowers are medium late, medium in size; and salmon in coloration.

Fruit:

*Maturity when described.*—Eating ripe — June 21.

*Size.*—Medium. Axial diameter — Approximately 1½ inch. Transverse in suture plane. — Approximately 1¾ inch. At right angles to suture plane — Approximately 1⅜ inch.

*Form.*—Uniform, symmetrical; round ovate.

*Suture.*—Shallow, distinct; extends from base to apex.

*Ventral surface.*—Rounded strong lipped towards base. Cavity: abrupt; free of markings; elongated in suture plane with suture showing on both sides; depth approximately 3/16 inch; breadth approximately 4/32 inch. Base: Cuneate and rounded. Apex: Rounded to truncate; apical. Stem: Medium stout; pubescent; approximately 5/16 inch in length; medium adherence to stone.

*Skin.*—Medium thickness; tenacious to flesh; slight tendency to break; down is moderately short and does not roll up when rubbed. Color: Orange Chrome Plate II, Color No. 11 of Ridgeway's Color Standards; highly blushed with Nopal Red Plate I, Color No. 3, tone i of Ridgeway's Color Standards.

*Flesh.*—Color: Orange yellow, Xanthine Orange Plate III, Color No. 13 tone i of Ridgeway's Color Standards; surface of pit cavity is white-yellow. Amygadalin: Moderate. Juice: Abundant and rich. Texture: Meaty. Fibers: Few, fine and tender. Ripens: Fairly evenly; first at apex along both lips. Flavor: Mild; subacid; and vinous. Aroma: Pronounced. Eating quality: Good.

*Stone.*—Freestone; adheres to flesh along dorsal edge. Size: Medium; approximately $1\frac{3}{8}$ inch in length and $\frac{1}{2}$ inch in thickness. Fibers: Short;

retain short fiber-like threads along ridges. Form: Cunate toward base and apex. Base: Straight; oval. Apex: Acute. Sides: Equal; curved on right and left sides. Surface Irregularly furrowed near ventral edge; pitted from base to above center. Ridges: Rounded and circular. Dorsal edge: Full, shallow narrow groove; ridges on either side are continuous. Kernal: Sweet edible almond-type.

Use: Dessert, canning.

Keeping quality: Medium good.

Resistance to insects: Medium.

Resistance to diseases: Medium.

Shipping quality: Medium good.

I claim:

1. A new and distinct variety of apricot tree, substantially as illustrated and described, characterized by (a) a medium-small spreading growth habit, (b) an extended bloom period, (c) enhanced spring frost tolerance, (d) abundantly forms deliciously flavored medium-sized fruit which is meaty textured and juicy and bears an attractive orange skin color having a bright red blush, and (e) forms a sweet edible almond-type kernel.

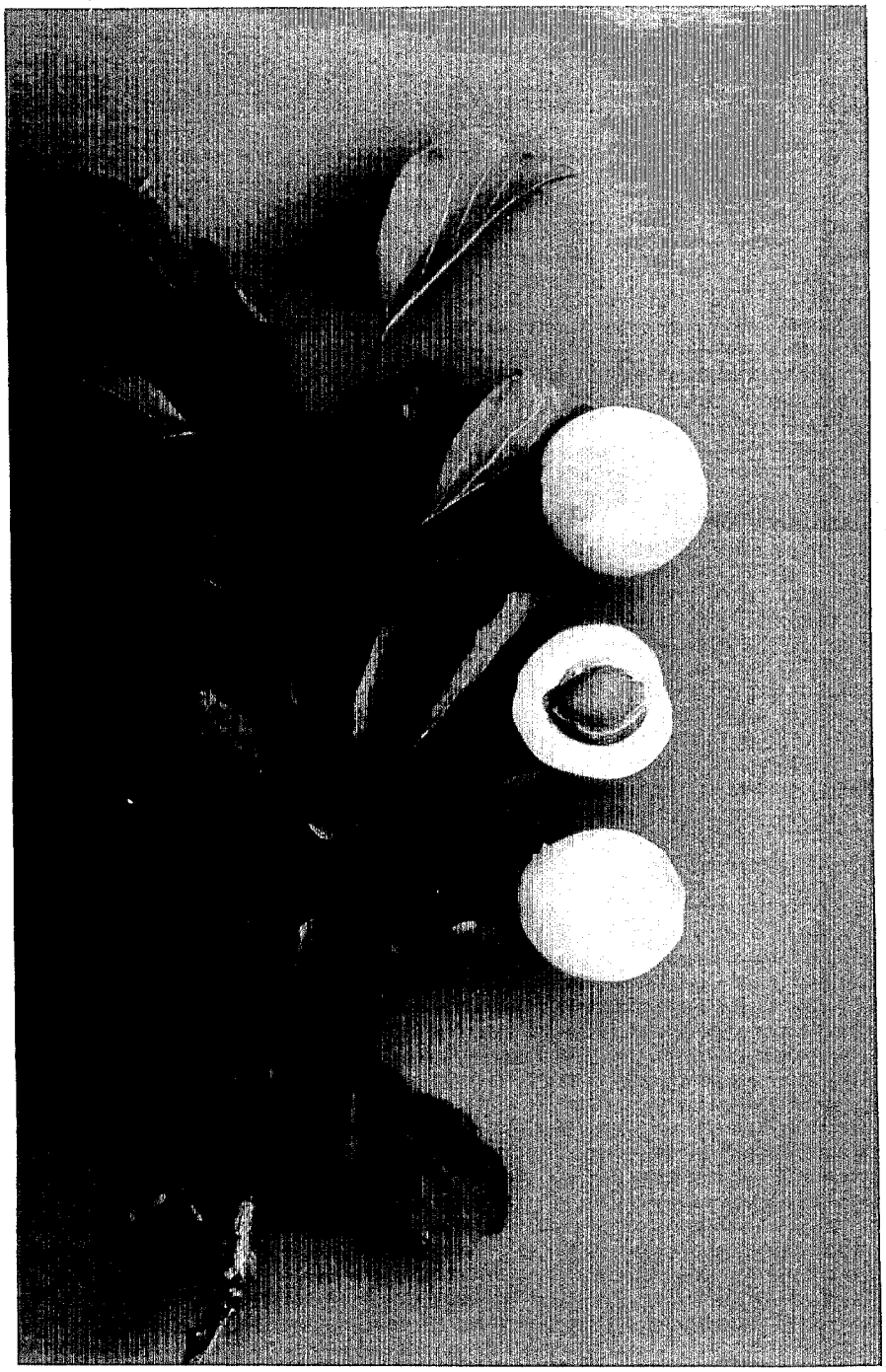

* * * * *